(12) United States Patent
Xu et al.

(10) Patent No.: US 10,710,236 B2
(45) Date of Patent: Jul. 14, 2020

(54) FLEXIBLE CONTINUUM STRUCTURE CAPABLE OF REALIZING POSTURE FEEDBACK

(71) Applicant: Beijing Surgerii Technology Co., Ltd., Shanghai (CN)

(72) Inventors: Kai Xu, Shanghai (CN); Jiangran Zhao, Shanghai (CN); Zhengchen Dai, Shanghai (CN); Huan Liu, Shanghai (CN); Zhixiong Yang, Shanghai (CN)

(73) Assignee: Beijing Surgerii Technology Co., Ltd., Beijing (CN)

( * ) Notice: Subject to any disclaimer, the term of this patent is extended or adjusted under 35 U.S.C. 154(b) by 0 days.

(21) Appl. No.: 16/289,040

(22) Filed: Feb. 28, 2019

(65) Prior Publication Data
US 2019/0193260 A1    Jun. 27, 2019

Related U.S. Application Data

(63) Continuation of application No. PCT/CN2017/099758, filed on Aug. 30, 2017.

(30) Foreign Application Priority Data

Aug. 31, 2016 (CN) .......................... 2016 1 0796046

(51) Int. Cl.
*B25J 1/02* (2006.01)
*A61B 34/30* (2016.01)
(Continued)

(52) U.S. Cl.
CPC ................. *B25J 1/02* (2013.01); *A61B 1/005* (2013.01); *A61B 17/00234* (2013.01);
(Continued)

(58) Field of Classification Search
None
See application file for complete search history.

(56) References Cited

U.S. PATENT DOCUMENTS

2006/0255758 A1* 11/2006 Takahashi ............ G05B 19/425
318/568.13
2013/0041509 A1* 2/2013 Saito .......................... B25J 9/06
700/261

(Continued)

*Primary Examiner* — Bentsu Ro
(74) *Attorney, Agent, or Firm* — Kilpatrick Townsend & Stockton LLP (57) ABSTRACT

A flexible continuum structure capable of realizing a posture feedback is provided. The flexible continuum structure can comprise a flexible continuum structure body and a posture feedback mechanism. The flexible continuum structure body can comprise a distal structural body, a proximal structural body and a middle connecting body. The distal structural body can comprise distal spacing disks, a distal fixation disk and distal structural backbones. The proximal structural body can comprise proximal spacing disks, a proximal fixation disk and proximal structural backbones. The middle connecting body can comprise a proximal guide channel fixing plate, a distal guide channel fixing plate and a structural backbone guide channel. One end of the structural backbone is connected to the proximal fixation disk, and the other end passes through the proximal spacing disks, the structural backbone guide channel and the distal spacing disks and is then securely connected to the distal fixation disk.

20 Claims, 8 Drawing Sheets

(51) Int. Cl.
  *B25J 19/02* (2006.01)
  *A61B 1/005* (2006.01)
  *A61B 17/00* (2006.01)

(52) U.S. Cl.
  CPC ............... *A61B 34/30* (2016.02); *B25J 19/02* (2013.01); *A61B 2017/00305* (2013.01); *A61B 2034/301* (2016.02)

(56) References Cited

U.S. PATENT DOCUMENTS

| | | | | |
|---|---|---|---|---|
| 2014/0084840 | A1* | 3/2014 | Osaka | G05B 19/404 318/632 |
| 2015/0045954 | A1* | 2/2015 | Negishi | B25J 9/06 700/262 |
| 2018/0290299 | A1* | 10/2018 | Kawaguchi | B25J 9/163 |
| 2020/0008874 | A1* | 1/2020 | Barbagli | A61M 25/01 |

* cited by examiner

FLEXIBLE CONTINUUM STRUCTURE CAPABLE OF REALIZING POSTURE FEEDBACK

CROSS REFERENCE TO RELATED APPLICATIONS

This patent application is a continuation of PCT Application No. PCT/CN2017/099758, filed on Aug. 30, 2017, which claims the priority of Chinese patent application No. 201610796046.8 filed on Aug. 31, 2016, entitled "Flexible Continuum Structure Capable of Realizing Posture Feedback", which is incorporated herein by reference in its entirety.

TECHNICAL FIELD

The present invention relates to a flexible continuum structure capable of realizing a posture feedback which can be applied to medical instruments, industrial automation equipment, etc.

BACKGROUND ART

In contrast to a traditional rigid kinematic chain which achieves a bending motion by rotating to each other at a joint, a flexible continuum mechanism achieves a bending deformation of a distal structure by the deformation of a proximal structure. In the flexible continuum mechanism, the main body of the structure is also a driving transfer structure, so that an extremely high degree of freedom configuration can be realized in a small-size space. The flexible continuum mechanism has the characteristics of a compact structure, high flexibility, flexible and safe contact guarantee, etc., and thus is widely used in the research and development of medical instruments, such as flexible manipulator arms, endoscopes and controllable catheters, and new special equipment such as industrial deep cavity detection endoscopes, and flexible robotic arms.

In the medical or industrial field, a distal end of the flexible continuum mechanism is mostly used to extend into a winding and complex deep cavity environment, the distal end thereof is mostly invisible or partially visible, and therefore, a posture feedback of the flexible continuum mechanism is an important safeguard for its reliability and safety of use. However, in the flexible continuum mechanism with a structural backbone as the main body, a bending motion thereof is realized by pushing and pulling the structural backbone. As the bending motion does not have a clear rotary joint, the feedback of a bending posture of the flexible continuum mechanism cannot be directly realized by an angle sensor disposed at the joint in the rigid kinematic chain, and at the same time, there is no posture feedback sensor especially for the flexible continuum mechanism.

SUMMARY OF THE INVENTION

In view of the above-mentioned problems, an object of the present invention is to provide a flexible continuum structure capable of realizing a posture feedback.

In order to achieve the above-mentioned object, the following technical solution is used for the present invention: a flexible continuum structure capable of realizing a posture feedback, comprising a flexible continuum structure body and a posture feedback mechanism; the flexible continuum structure body comprises a distal structural body, a proximal structural body and a middle connecting body; the distal structural body comprises distal spacing disks, a distal fixation disk and distal structural backbones; the proximal structural body comprises proximal spacing disks, a proximal fixation disk and proximal structural backbones; the proximal structural backbones are securely connected, in one-to-one correspondence, to or are the same as the distal structural backbones; the middle connecting body comprises a proximal guide channel fixing plate, a distal guide channel fixing plate and a structural backbone guide channel, and the structural backbone guide channel is securely connected between the proximal guide channel fixing plate and the distal guide channel fixing plate; one end of the structural backbone is securely connected to the proximal fixation disk, and the other end passes through the proximal spacing disks, the structural backbone guide channel and the distal spacing disks in sequence and is then securely connected to the distal fixation disk; the posture feedback mechanism comprises one or more of an identical posture feedback structure, a first proportional feedback structure and a second proportional feedback structure; the identical posture feedback structure comprises second distal spacing disks, a second distal fixation disk, second distal structural backbones, second proximal structural backbones and a second structural backbone guide channel; the second structural backbone guide channel is securely connected between the proximal guide channel fixing plate and the distal guide channel fixing plate, the second proximal structural backbones are securely connected, in one-to-one correspondence, to or are the same as the second distal structural backbones, one end of the second structural backbone is securely connected to the proximal fixation disk, and the other end passes through the proximal spacing disks, the second structural backbone guide channel and the second distal spacing disks in sequence and is then securely connected to the second distal fixation disk; the ratio of the distribution radius of the second distal structural backbone to that of the second proximal structural backbone is consistent with the ratio of the distribution radius of the distal structural backbone to that of the proximal structural backbone; the length of the identical posture feedback structure is consistent with that of the distal structural body; the first proportional feedback structure comprises third distal spacing disks, a third distal fixation disk, third distal structural backbones, third proximal structural backbones and a third structural backbone guide channel; the third structural backbone guide channel is securely connected between the proximal guide channel fixing plate and the distal guide channel fixing plate, the third proximal structural backbones are securely connected, in one-to-one correspondence, to or are the same as the third distal structural backbones, one end of the third structural backbone is securely connected to the proximal fixation disk, and the other end passes through the proximal spacing disks, the third structural backbone guide channel and the third distal spacing disks in sequence and is then securely connected to the third distal fixation disk; the ratio of the distribution radius of the third distal structural backbone to that of the third proximal structural backbone is different from the ratio of the distribution radius of the distal structural backbone to that of the proximal structural backbone; the second proportional feedback structure comprises fourth distal spacing disks, a fourth distal fixation disk, fourth distal structural backbones, fourth proximal structural backbones and a fourth structural backbone guide channel; the fourth structural backbone guide channel is securely connected between the proximal guide channel fixing plate and the distal guide channel fixing plate, the fourth proximal structural backbones are securely connected, in one-to-one correspondence, to or are the same as the fourth distal structural backbones, one end of the fourth structural backbone is securely connected to the proximal fixation disk, and the other end passes through the proximal spacing disks, the fourth structural backbone guide channel and the fourth distal spacing disks in sequence and is then securely connected to the fourth distal fixation disk; and each of the fourth distal structural backbones and the corresponding fourth proximal structural backbone, which have a connection relationship, have spacing angles on the circumference between each other, with the degree of the spacing angles being the same.

In an embodiment, the flexible continuum structure body further comprises an articulated driving chain, which comprising a rotating base and a driving handle, with the rotating base being rotatably connected in the center of the proximal guide channel fixing plate, and the axis of rotation of the rotating base being perpendicular to the proximal guide channel fixing plate; and the driving handle is of a rod structure and a front end thereof is rotatably connected to the rotating base, the axis of rotation of which is parallel to the proximal guide channel fixing plate, and the driving handle slidably and rotatably passes through the center of the proximal fixation disk.

In an embodiment, the middle connecting body further comprises a rigid tube, the rigid tube is securely connected to the side of the distal guide channel fixing plate that is close to the distal structural body, the rigid tube is internally provided with a cavity in communication with the structural backbone guide channel, and the structural backbones pass through the cavity.

In an embodiment, when the posture feedback mechanism comprises an identical posture feedback structure, the identical posture feedback structure further comprises a second rigid tube, and the second structural backbones pass through the second rigid tube; when the posture feedback mechanism comprises a first proportional feedback structure, the first proportional feedback structure further comprises a third rigid tube, and the third structural backbones pass through the third rigid tube; and when the posture feedback mechanism comprises a second proportional feedback structure, the second proportional feedback structure further comprises a fourth rigid tube, and the fourth structural backbones pass through the fourth rigid tube.

In an embodiment, the posture feedback mechanism further comprises a posture measurement assembly, which comprising a distal feedback structural backbone, a feedback structural backbone guide channel and a position sensor; and the position sensor is securely connected to the proximal guide channel fixing plate, one end of the distal feedback structural backbone is securely connected to the distal fixation disk, and the other end passes through the distal spacing disks and the feedback structural backbone guide channel and is then connected to the position sensor.

In an embodiment, a third guide channel fixing plate is provided between the proximal guide channel fixing plate and the distal guide channel fixing plate, and the feedback structural backbone guide channel is securely connected between the third guide channel fixing plate and the distal guide channel fixing plate.

In an embodiment, the posture feedback mechanism further comprises a posture measurement assembly, which comprising a proximal feedback structural backbone and a position sensor, the position sensor is securely connected to the proximal guide channel fixing plate, one end of the proximal feedback structural backbone is securely connected to the proximal fixing plate, and the other end passes through the proximal spacing disks and is then connected to the position sensor.

In an embodiment, the posture feedback mechanism further comprises a posture measurement assembly, which comprising a first joint angle sensor and a second joint angle sensor, wherein the first joint angle sensor is used for measuring the relative rotation angle between the rotating base and the proximal guide channel fixing plate, and the second joint angle sensor is used for measuring the relative rotation angle between the driving handle and the rotating base.

In an embodiment, the posture feedback mechanism further comprises a posture measurement assembly, which comprising three or more distance sensors mounted on the proximal guide channel fixing plate for measuring the distance of specific points on the proximal fixation disk.

In an embodiment, the position sensor uses a slider linear position sensor.

According to another aspect of the present invention, further provided is a flexible continuum structure capable of realizing a posture feedback, comprising a flexible continuum structure body and a posture feedback mechanism;

the flexible continuum structure body comprises a distal structural body, a proximal structural body and a middle connecting body; the distal structural body comprises distal spacing disks, a distal fixation disk and distal structural backbones; the proximal structural body comprises proximal spacing disks, a proximal fixation disk and proximal structural backbones; the proximal structural backbones being securely connected, in one-to-one correspondence, to or being the same as the distal structural backbones; the middle connecting body comprising a proximal guide channel fixing plate, a distal guide channel fixing plate and a structural backbone guide channel, and the structural backbone guide channel being securely connected between the proximal guide channel fixing plate and the distal guide channel fixing plate; one end of the structural backbone being securely connected to the proximal fixation disk, and the other end passing through the proximal spacing disks, the structural backbone guide channel and the distal spacing disks in sequence and being then securely connected to the distal fixation disk; and the posture feedback mechanism comprises one or more of an identical posture feedback structure, a first proportional feedback structure and a second proportional feedback structure; wherein, the identical posture feedback structure comprises a second distal fixation disk, second distal structural backbones, second proximal structural backbones and a second structural backbone guide channel; the second structural backbone guide channel is securely connected between the proximal guide channel fixing plate and the distal guide channel fixing plate, the second proximal structural backbones are securely connected, in one-to-one correspondence, to or are the same as the second distal structural backbones, one end of the second structural backbone is securely connected to the proximal fixation disk, and the other end passes through the proximal spacing disks and the second structural backbone guide channel in sequence and is then securely connected to the second distal fixation disk; the ratio of the distribution radius of the second distal structural backbone to that of the second proximal structural backbone is consistent with the ratio of the distribution radius of the distal structural backbone to that of the proximal structural backbone;

the first proportional feedback structure comprises a third distal fixation disk, third distal structural backbones, third proximal structural backbones and a third structural backbone guide channel; the third structural backbone guide channel is securely connected between the proximal guide channel fixing plate and the distal guide channel fixing plate, the third proximal structural backbones are securely connected, in one-to-one correspondence, to or are the same as the third distal structural backbones, one end of the third structural backbone is securely connected to the proximal fixation disk, and the other end passes through the proximal spacing disks and the third structural backbone guide channel in sequence and is then securely connected to the third distal fixation disk; the ratio of the distribution radius of the third distal structural backbone to that of the third proximal structural backbone is different from the ratio of the distribution radius of the distal structural backbone to that of the proximal structural backbone;

the second proportional feedback structure comprises a fourth distal fixation disk, fourth distal structural backbones, fourth proximal structural backbones and a fourth structural backbone guide channel; the fourth structural backbone guide channel is securely connected between the proximal guide channel fixing plate and the distal guide channel fixing plate, the fourth proximal structural backbones are securely connected, in one-to-one correspondence, to or are the same as the fourth distal structural backbones, one end of the fourth structural backbone is securely connected to the proximal fixation disk, and the other end passes through the proximal spacing disks and the fourth structural backbone guide channel in sequence and is then securely connected to the fourth distal fixation disk; and each of the fourth distal structural backbones and the corresponding fourth proximal structural backbone, which have a connection relationship, have spacing angles on the circumference between each other, with the degree of the spacing angles being the same.

In an embodiment, when the posture feedback mechanism comprises an identical posture feedback structure, the identical posture feedback structure is further provided with second distal spacing disks, and the other end of the second structural backbone further passes through the second distal spacing disks after passing through the second structural backbone guide channel and is then securely connected to the second distal fixation disk; when the posture feedback mechanism comprises a first proportional feedback structure, the first proportional feedback structure is further provided with third distal spacing disks, and the other end of the third structural backbone further passes through the third distal spacing disks after passing through the third structural backbone guide channel and is then securely connected to the third distal fixation disk; and when the posture feedback mechanism comprises a second proportional feedback structure, the second proportional feedback structure is further provided with fourth distal spacing disks, and the other end of the fourth structural backbone further passes through the fourth distal spacing disks after passing through the fourth structural backbone guide channel and is then securely connected to the fourth distal fixation disk.

In another embodiment, when the posture feedback mechanism comprises an identical posture feedback structure, the identical posture feedback structure is further provided with second distal spacing disks, and the other end of the second structural backbone further passes through the second distal spacing disks after passing through the second structural backbone guide channel and is then securely connected to the second distal fixation disk; and the length of the identical posture feedback structure is consistent with that of the distal structural body.

Preferably, the flexible continuum structure body further comprises an articulated driving chain, which comprising a rotating base and a driving handle, with the rotating base being rotatably connected in the center of the proximal guide channel fixing plate, and the axis of rotation of the rotating base being perpendicular to the proximal guide channel fixing plate; and the driving handle is rotatably connected to the rotating base, the axis of rotation of which is parallel to the proximal guide channel fixing plate, and the driving handle slidably and rotatably passes through the center of the proximal fixation disk.

Preferably, the middle connecting body further comprises a rigid tube, the rigid tube is securely connected to the side of the distal guide channel fixing plate that is close to the distal structural body, the rigid tube is internally provided with a cavity in communication with the structural backbone guide channel, and the structural backbone passes through the cavity.

According to still another aspect of the present invention, further provided is a flexible continuum structure capable of realizing a posture feedback, the flexible continuum structure comprising a flexible continuum structure body and a posture feedback mechanism, wherein, the flexible continuum structure body comprises a distal structural body, a proximal structural body and a middle connecting body; the distal structural body comprises distal spacing disks, a distal fixation disk and distal structural backbones; the proximal structural body comprises proximal spacing disks, a proximal fixation disk and proximal structural backbones; the proximal structural backbones are securely connected, in one-to-one correspondence, to or being the same as the distal structural backbones; the middle connecting body comprises a proximal guide channel fixing plate, a distal guide channel fixing plate and a structural backbone guide channel, and the structural backbone guide channel is securely connected between the proximal guide channel fixing plate and the distal guide channel fixing plate; one end of the structural backbone is securely connected to the proximal fixation disk, and the other end passes through the proximal spacing disks, the structural backbone guide channel and the distal spacing disks in sequence and is then securely connected to the distal fixation disk; and the posture feedback mechanism comprises a posture measurement assembly, which is configured to be able to detect a bending angle value and a length value of the distal structural body.

In an embodiment, the posture measurement assembly comprises a distal feedback structural backbone, a feedback structural backbone guide channel and a position sensor; and the position sensor is securely connected to the proximal guide channel fixing plate, one end of the distal feedback structural backbone is securely connected to the distal fixation disk, and the other end passes through the distal spacing disks and the feedback structural backbone guide channel and is then connected to the position sensor.

In another embodiment, the posture measurement assembly comprises a proximal feedback structural backbone and a position sensor, the position sensor is securely connected to the proximal guide channel fixing plate, one end of the proximal feedback structural backbone is securely connected to the proximal fixation plate, and the other end passes through the proximal spacing disks and is then connected to the position sensor.

Preferably, the flexible continuum structure body further comprises an articulated driving chain, which comprising a rotating base and a driving handle, with the rotating base being rotatably connected in the center of the proximal guide channel fixing plate, and the axis of rotation of the rotating base being perpendicular to the proximal guide channel fixing plate; and the driving handle is rotatably connected to the rotating base, the axis of rotation of which is parallel to the proximal guide channel fixing plate, and the driving handle slidably and rotatably passes through the center of the proximal fixation disk.

In another embodiment, the posture feedback mechanism comprises a first joint angle sensor and a second joint angle sensor, wherein the first joint angle sensor is used for measuring the relative rotation angle between the rotating base and the proximal guide channel fixing plate, and the second joint angle sensor is used for measuring the relative rotation angle between the driving handle and the rotating base.

In another embodiment, the posture measurement assembly comprises three or more distance sensors mounted on the proximal guide channel fixing plate for measuring the distance of specific points on the proximal fixation disk.

The present invention adopts the above technical solutions, and has the following advantages: 1. the present invention proposes a manually driven flexible continuum structure with a distal end being able to turn in any arbitrary direction, the flexible continuum structure comprising a distal structural body, a middle connecting body, a proximal structural body and an articulated driving chain, wherein the distal structural body is associated with the proximal structural body via the middle connecting body, and therefore, the proximal structural body can be driven to turn in any arbitrary direction via the articulated driving chain, thus the distal structural body turns in an opposite direction; 2. the present invention is provided with a posture feedback mechanism comprising one or more feedback structural bodies, and therefore, posture feedbacks of the distal structural body and the proximal structural body can be achieved by a visible feedback structure which is associated with the proximal structural body and has a certain relationship with the distal structural body in the bending angle and the length; 3. the present invention is provided with a posture measurement assembly comprising a distal feedback structural backbone and a position sensor, and therefore, posture measurement of the distal structural body and the proximal structural body can be achieved by measuring the change of length of the distal feedback structural backbone in the distal structural body; 4. the present invention is provided with a posture measurement assembly comprising a proximal feedback structural backbone and a position sensor, and therefore, posture measurement of the distal structural body and the proximal structural body can be achieved by measuring the change of length of the proximal feedback structural backbone in the proximal structural body; 5. the present invention is provided with a posture measurement assembly comprising a first joint angle sensor and a second joint angle sensor, and therefore, posture measurement of the distal structural body and the proximal structural body can be achieved by measuring a joint angle value of the articulated driving chain; 6. the present invention is provided with a posture measurement assembly comprising a distance sensor, and therefore, posture measurement of the distal structural body and the proximal structural body can be achieved by measuring spatial positions of several specific points on the proximal fixation disk.

DETAILED DESCRIPTION OF EMBODIMENTS

The present invention is described in detail below in conjunction with the accompanying drawings and embodiments.

Figure 1:
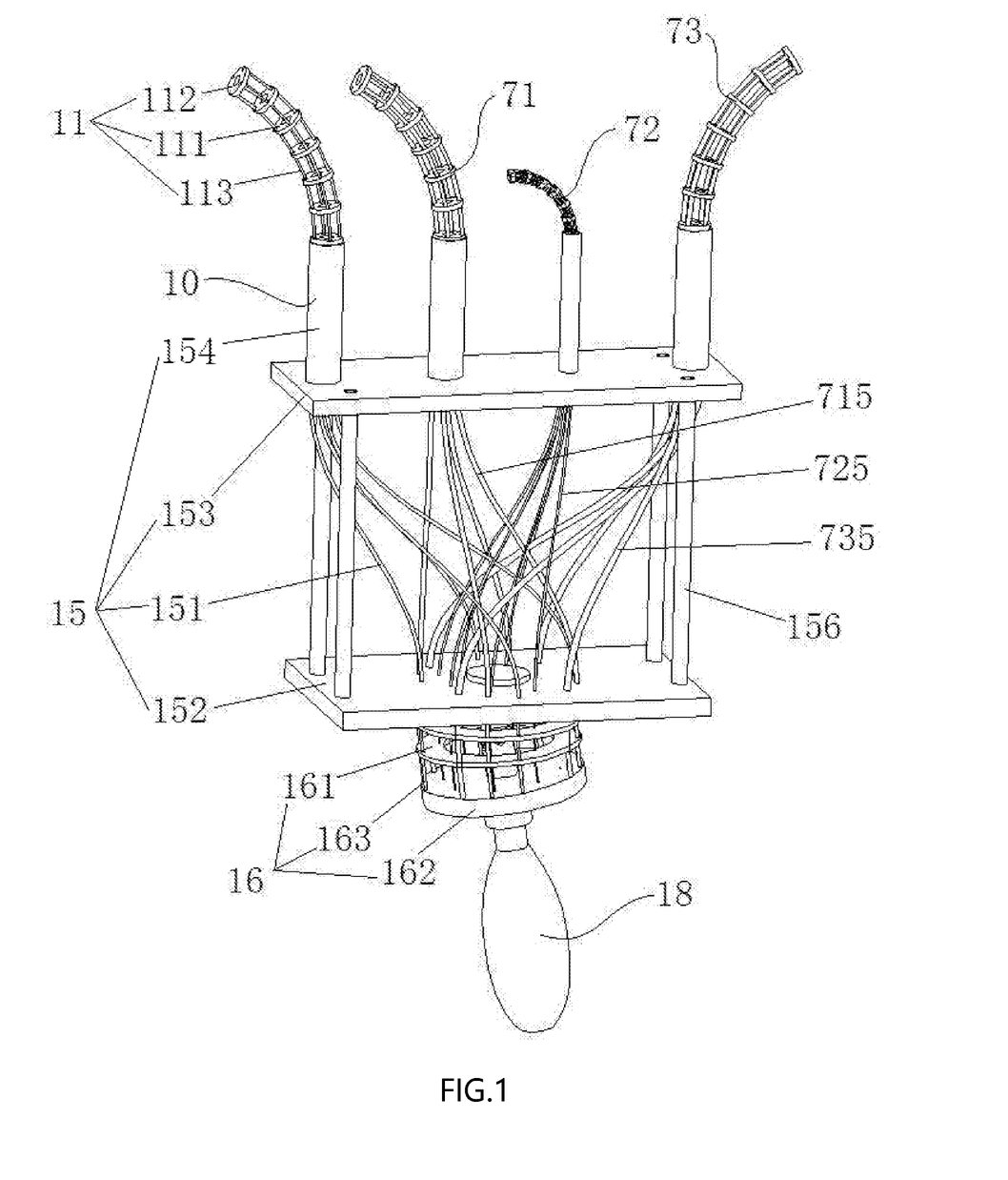
FIG. 1 is an overall structural schematic diagram of the present invention.
Figure 2:
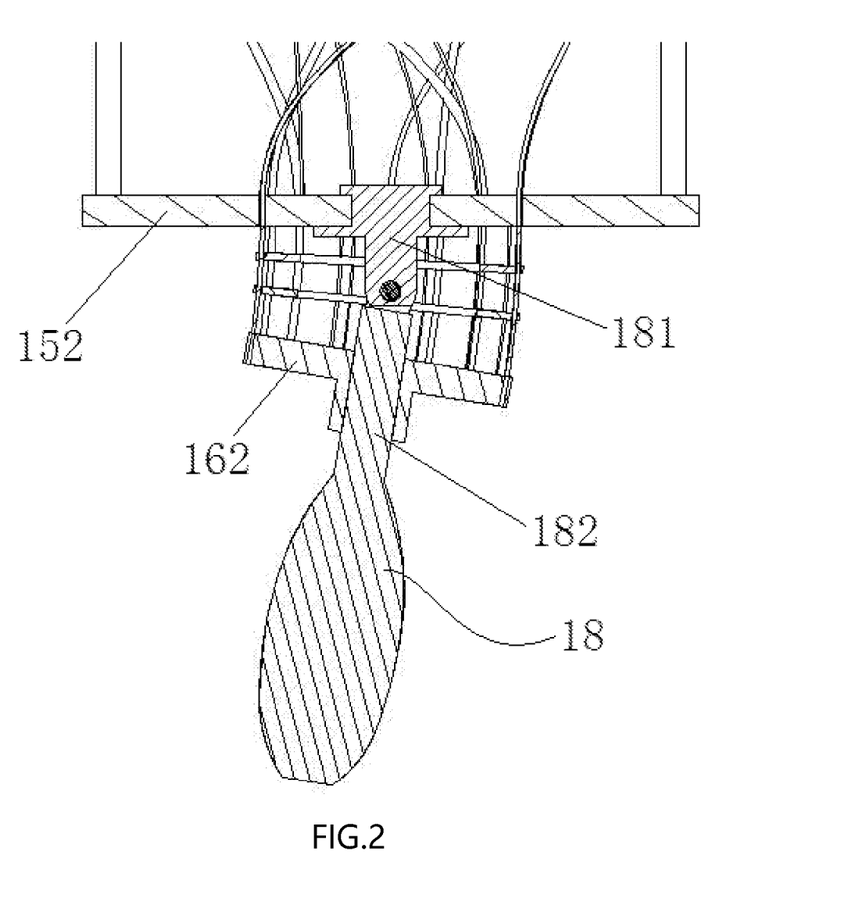
FIG. 2 is a structural schematic diagram of an articulated driving chain according to the present invention.

As shown in FIGS. 1 and 2, the present invention comprises a flexible continuum structure body 10 and a posture feedback mechanism.

The flexible continuum structure body 10 of the present invention comprises a distal structural body 11, a middle connecting body 15, a proximal structural body 16 and an articulated driving chain 18. The distal structural body 11 comprises distal spacing disks 111, a distal fixation disk 112 and distal structural backbones 113, wherein the distal spacing disks 111 are distributed in the distal structural body 11 at intervals, and function to prevent the instability of the distal structural backbones 113 when pushed. The proximal structural body 16 comprises proximal spacing disks 161, a proximal fixation disk 162 and proximal structural backbones 163, wherein the proximal spacing disks 161 are distributed in the proximal structural body 16 at intervals, and function to prevent the instability of the proximal structural backbones 163 when pushed. The proximal structural backbones 163 in the proximal structural body 16 are securely connected, in one-to-one correspondence, to or are the same as the distal structural backbones 113 in the distal structural body 11. Three or more structural backbones are provided for each of the proximal structural body 16 and the distal structural body 11. The middle connecting body 15 comprises a proximal guide channel fixing plate 152, a distal guide channel fixing plate 153, a structural backbone guide channel 151 and a rigid tube 154, wherein the structural backbone guide channel 151 is securely connected between the proximal guide channel fixing plate 152 and the distal guide channel fixing plate 153, and the rigid tube 154 is securely connected to the side of the distal guide channel fixing plate 153 that is close to the distal structural body 11. One end of the structural backbone is securely connected to the proximal fixation disk 162, and the other end passes through the proximal spacing disks 161, the structural backbone guide channel 151, the rigid tube 154 and the distal spacing disks 111 in sequence and is then securely connected to the distal fixation disk 112. The structural backbone guide channel 151 functions to maintain the shape of the structural backbone under a pushing or pulling force.

The articulated driving chain 18 comprises a rotating base 181 and a driving handle 182, wherein the rotating base 181 is rotatably connected in the center of the proximal guide channel fixing plate 152, and the axis of rotation is perpendicular to the plane where the proximal guide channel fixing plate 152 is located; and the driving handle 182 is of a rod structure and a front end thereof is rotatably connected to the rotating base 181, the axis of rotation of which is parallel the proximal guide channel fixing plate 152, the driving handle 182 slidably and rotatably passes through the center of the proximal fixation disk 162, the axis of the driving handle 182 is perpendicular to the proximal fixation disk 162, and a rear end of the driving handle 182 is provided with a handle that is easy to hold. When the driving handle 182 turns in any arbitrary direction in the space, the proximal fixation disk 162 is driven to turn in the same direction, and the section profile of the proximal structural body 16 in a bending plane is kept in an approximately circular arc shape, then the proximal structural backbones 163 in the proximal structural body 16 are pushed and pulled such that the length of the proximal structural backbones in the proximal structural body 16 changes, thereby the distal structural body 11 bending in an opposite direction in a certain proportion (this proportion being determined jointly by the distribution radii of the distal structural backbone 113 and the proximal structural backbone 163).

The posture feedback mechanism of the present invention comprises one or more feedback structural bodies, and the feedback structure can be an identical posture feedback structure 71, a first proportional feedback structure 72 or a second proportional feedback structure 73.

Figure 3:
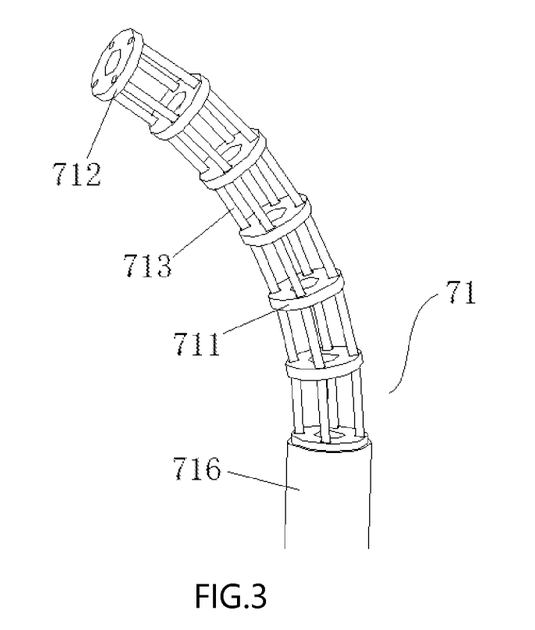
FIG. 3 is a structural schematic diagram of an identical posture feedback structure according to the present invention.
Figure 6:
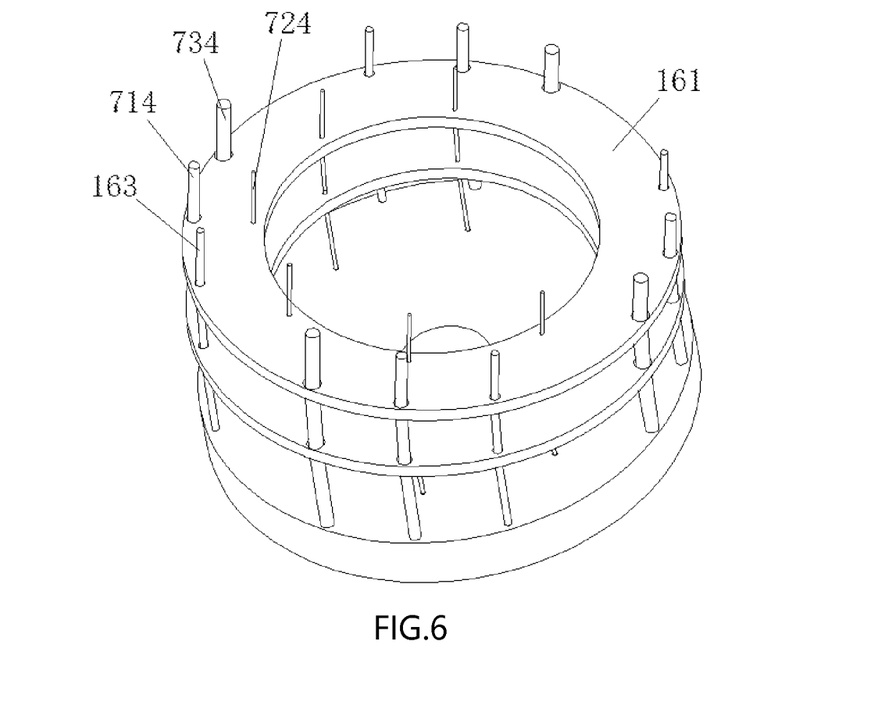
FIG. 6 is a structural schematic diagram of a proximal structural body according to the present invention.

As shown in FIGS. 1, 3 and 6, the identical posture feedback structure 71 comprises second distal spacing disks 711, a second distal fixation disk 712, second distal structural backbones 713, second proximal structural backbones 714, a second structural backbone guide channel 715 and a second rigid tube 716, wherein the second structural backbone guide channel 715 is securely connected between the proximal guide channel fixing plate 152 and the distal guide channel fixing plate 153, and the second proximal structural backbones 714 are securely connected, in one-to-one correspondence, to or are the same as the second distal structural backbones 713. One end of the structural backbone is securely connected to the proximal fixation disk 162, and the other end passes through the proximal spacing disks 161, the second structural backbone guide channel 715, the second rigid tube 716 and the second distal spacing disks 711 in sequence and is then securely connected to the second distal fixation disk 712. The ratio of the distribution radius of the second distal structural backbone 713 to that of the second proximal structural backbone 714 is consistent with the ratio of the distribution radius of the distal structural backbone 113 to that of the proximal structural backbone 163; and the length of the identical posture feedback structure 71 is consistent with that of the distal structural body 11. Thereby, when the proximal structural body 16 is driven to turn, the identical posture feedback structure 71 turns, and a bending angle (including a bending plane orientation angle and a bending angle in the bending plane) and the length are consistent with the distal structural body 11. It should be noted that the thickness and number of the second distal structural backbones 713 in the identical posture feedback structure 71 and the second proximal structural backbones 714, and the circumferential distribution angle of the structural backbones in the corresponding spacing disks and fixation disk can be different from that of the corresponding distal structural backbones 113 and proximal structural backbones 163. The shape of the second distal spacing disks 711 in the identical posture feedback structure 71 can be different from the distal spacing disks 111 in the distal structural body 11.

Figure 4:
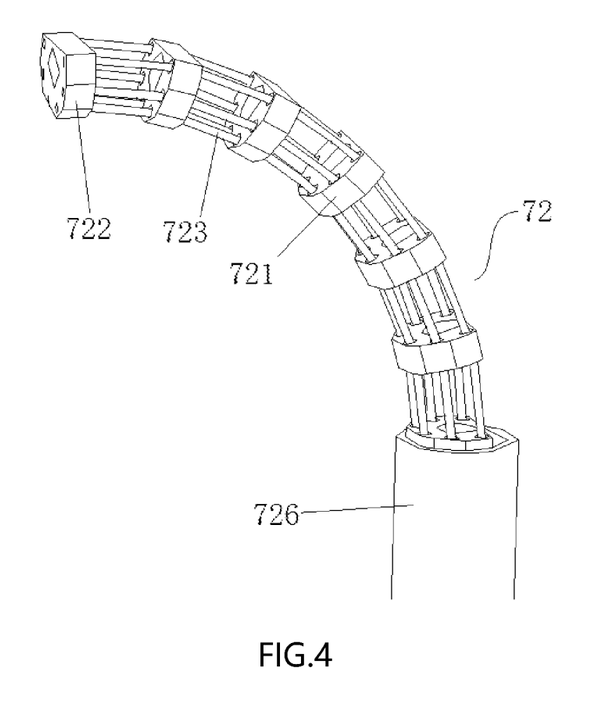
FIG. 4 is a structural schematic diagram of a first proportional feedback structure according to the present invention.

As shown in FIGS. 1, 4 and 6, the first proportional feedback structure 72 comprises third distal spacing disks 721, a third distal fixation disk 722, third distal structural backbones 723, third proximal structural backbones 724, a third structural backbone guide channel 725 and a third rigid tube 726, wherein the third structural backbone guide channel 725 is securely connected between the proximal guide channel fixing plate 152 and the distal guide channel fixing plate 153, and the third proximal structural backbones 724 are securely connected, in one-to-one correspondence, to or are the same as the third distal structural backbones 723. One end of the structural backbone is securely connected to the proximal fixation disk 162, and the other end passes through the proximal spacing disks 161, the third structural backbone guide channel 725, the third rigid tube 726 and the third distal spacing disks 721 in sequence and is then securely connected to the third distal fixation disk 722. The number, thickness and distribution radius of the third distal structural backbones 723 in the first proportional feedback structure 72 and the third proximal structural backbones 724, and the circumferential distribution angle of the structural backbones in the corresponding spacing disks and fixation disk can be different from that of the corresponding distal structural backbones 113 and proximal structural backbones 163. Therefore, when the proximal structural body 16 is driven to turn, the distal structural body 11 turns in an opposite direction, while the bending motion of the first proportional feedback structure 72 has the same bending plane orientation as that of the distal structural body 11 but different bending angles in the bending plane, this bending angle is in a fixed proportional coefficient to the bending angle of the distal structural body 11 in the bending plane, and the proportional coefficient is determined jointly by the distribution radii of the distal structural backbone 113, the proximal structural backbone 163, the third distal structural backbone 723 and the third proximal structural backbone 724.

Figure 5:
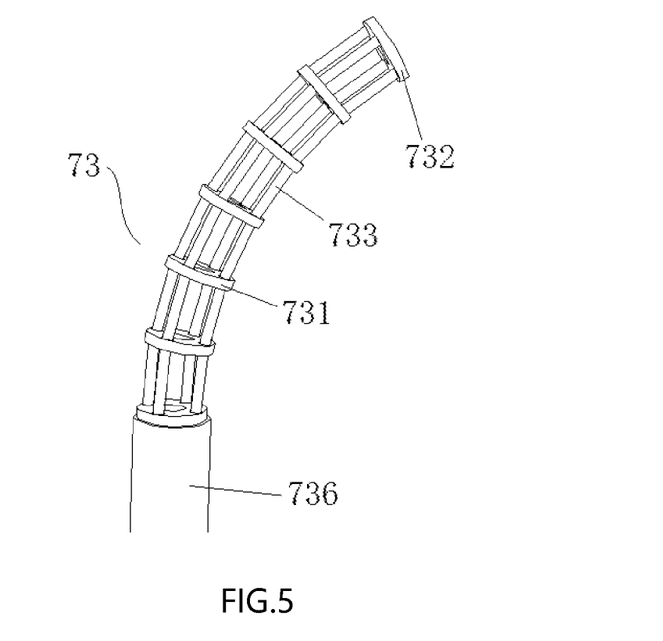
FIG. 5 is a structural schematic diagram of a second proportional feedback structure according to the present invention.

As shown in FIGS. 1, 5 and 6, the second proportional feedback structure 73 comprises fourth distal spacing disks 731, a fourth distal fixation disk 732, fourth distal structural backbones 733, fourth proximal structural backbones 734, a fourth structural backbone guide channel 735 and a fourth rigid tube 736, wherein the fourth structural backbone guide channel 735 is securely connected between the proximal guide channel fixing plate 152 and the distal guide channel fixing plate 153, and the fourth proximal structural backbones 734 are securely connected, in one-to-one correspondence, to or are the same as the fourth distal structural backbones 733. One end of the structural backbone is securely connected to the proximal fixation disk 162, and the other end passes through the proximal spacing disks 161, the fourth structural backbone guide channel 735, the fourth rigid tube 736 and the fourth distal spacing disks 731 in sequence and is then securely connected to the fourth distal fixation disk 732. The number and thickness of the fourth distal structural backbones 733 in the second proportional feedback structure 73 and the fourth proximal structural backbones 734, and the circumferential distribution angle of the structural backbones in the corresponding spacing disks and fixation disk can be different from that of the corresponding distal structural backbones 113 and proximal structural backbones 163. Further, each of the fourth distal structural backbones 733 and the corresponding fourth proximal structural backbone 734, which have a connection relationship, have spacing angles on the circumference, with the degree of the spacing angles being the same. Thereby, when the proximal structural body 16 is driven to turn, the distal structural body 11 turns in an opposite direction, while the bending plane orientation angle of the second proportional feedback structure 73 is determined by the degree of the above-mentioned spacing angles. Preferably, when the spacing angle is 180°, the bending plane orientation of the second proportional feedback structure 73 is opposite that of the distal structural body 11, and the bending of the second proportional feedback structure 73 is mirrored to that of the proximal structural body 16.

In practical engineering, one or more of the above-mentioned identical posture feedback structure 71, the first proportional feedback structure 72 and the second proportional feedback structure 73 can be provided according to actual requirements, and a viewer can infer actual postures of the distal structural body 11 and the proximal structural body 16 from a feedback structure in a visible position. Further, the above-mentioned identical posture feedback structure, the first proportional feedback structure and the second proportional feedback structure can also achieve the above effects without providing the distal spacing disks.

Further, the rigid tube 154 is provided with a cavity for guiding the structural backbones and in communication with the structural backbone guide channel 151. It should be appreciated by those skilled in the art that the cavity for guiding the structural backbones can also be formed by structural backbone through holes which are distributed at intervals in the distal spacing disks 111 in the rigid tube 154.

Further, the proximal guide channel fixing plate 152 is connected to the distal guide channel fixing plate 153 directly by a plurality of support columns 156.

In the above-mentioned embodiment, the posture feedback mechanism further comprises a posture measurement assembly, which is used for measuring a bending angle value and a length value of the distal structural body 11 and the proximal structural body 16 to thus accurately achieve posture parameters of the flexible continuum structure body 10. The present invention proposes a plurality of posture measurement assemblies, which are respectively described as below:

Embodiment I

Figure 7:
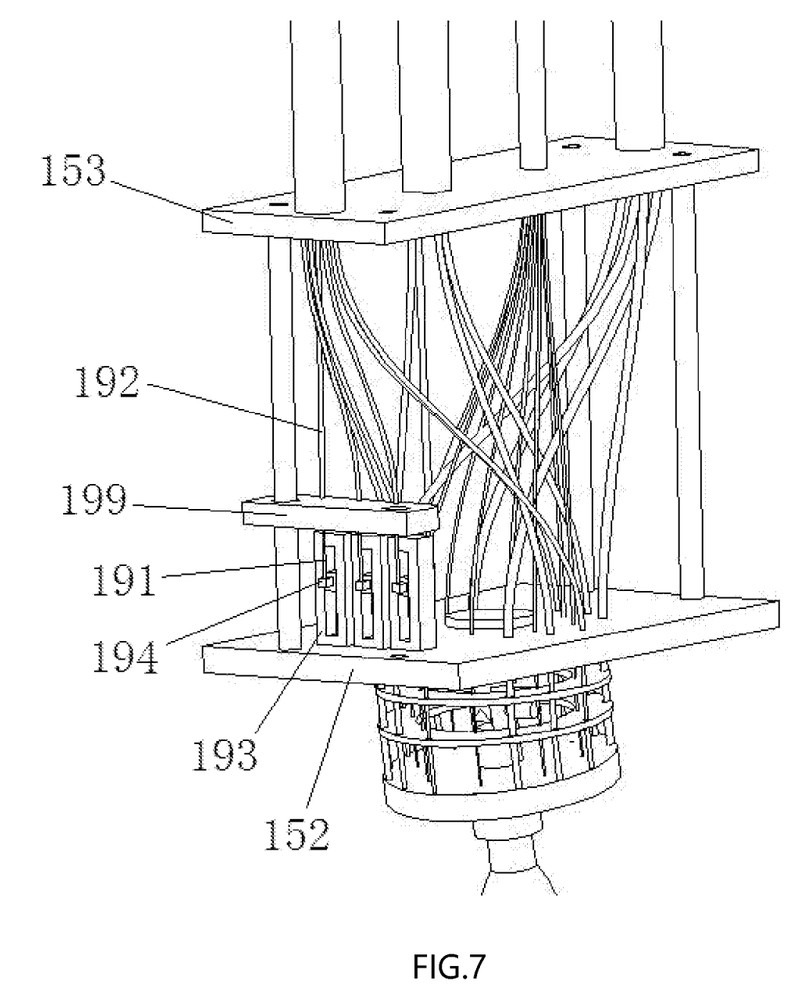
FIG. 7 is a structural schematic diagram of a first posture measurement assembly according to the present invention.

As shown in FIG. 7, the posture measurement assembly in this embodiment comprises a distal feedback structural backbone 191, a feedback structural backbone guide channel 192 and a position sensor 193, wherein the position sensor 193 is fixedly connected to a proximal guide channel fixing plate 152, one end of the distal feedback structural backbone 191 is securely connected to a distal fixation disk 112, and the other end passes through distal spacing disks 111, a rigid tube 154 and the feedback structural backbone guide channel 192 in sequence and is then connected to the position sensor 193. In this embodiment, when a distal structural body 11 turns, the length of the distal feedback structural backbone 191 in the distal structural body 11 changes, thereby a connecting end of the distal feedback structural backbone 191 and the position sensor 193 is displaced, which is detected by the position sensor 193. By measuring the length of three or more non-coplanar distal feedback structural backbones 191 distributed in the distal structural body 11, a bending angle value and a length value of the distal structural body 11 can be calculated, wherein the bending angle value comprises a bending plane orientation angle value of the distal structural body 11 and a bending angle value of same in the bending plane, and then a bending angle value and a length value of a proximal structural body 16 can be obtained according to the distribution radii and the lengths of distal structural backbones 113 and proximal structural backbones 163.

Further, the position sensor 193 uses a slider linear position sensor, and a sliding block 194 in the position sensor 193 is securely connected to the distal feedback structural backbone 191.

Further, a third guide channel fixing plate 199 is provided between the proximal guide channel fixing plate 152 and a distal guide channel fixing plate 153, one end of the feedback structural backbone guide channel 192 is securely connected to the distal guide channel fixing plate 153, and the other end is securely connected to the third guide channel fixing plate 199.

Embodiment II

Figure 8:
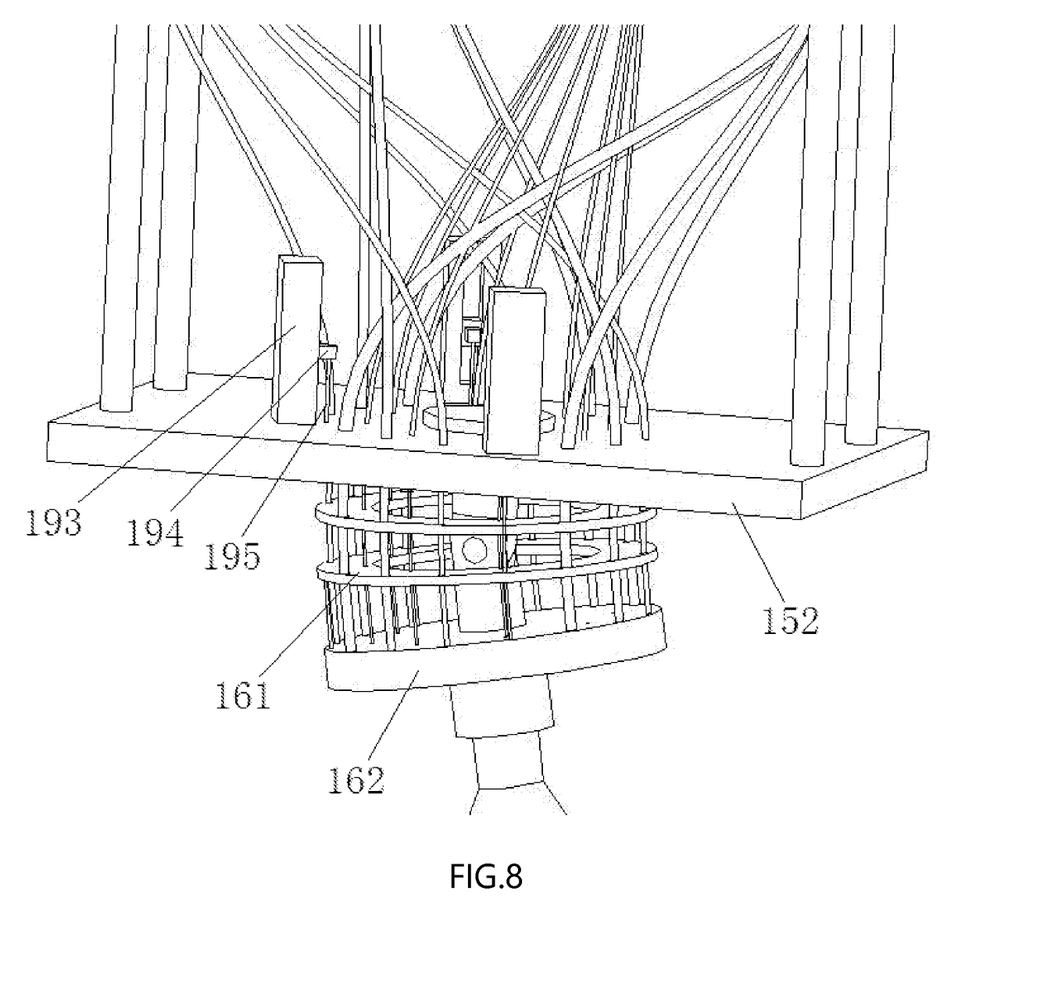
FIG. 8 is a structural schematic diagram of a second posture measurement assembly according to the present invention.

As shown in FIG. 8, a posture measurement assembly in this embodiment comprises a proximal feedback structural backbone 195 and a position sensor 193, wherein the position sensor 193 is fixedly connected to a proximal guide channel fixing plate 152, one end of the proximal feedback structural backbone 195 is securely connected to a proximal fixation disk 162, and the other end passes through proximal spacing disks 161 and the proximal guide channel fixing plate 152 and is then connected to the position sensor 193. In this embodiment, the bending motion of a proximal structural body 16 changes the length of the proximal feedback structural backbone 195 in the proximal structural body 16, thereby a connecting end of the proximal feedback structural backbone 195 and the position sensor 193 is displaced, which is detected by the position sensor 193. By measuring the length of three or more non-coplanar proximal feedback structural backbones 195 distributed in the proximal structural body 16, the bending angle value and the length value of the proximal structural body 16 can be calculated, wherein the bending angle value comprises a bending plane orientation angle value of the proximal structural body 16 and a bending angle value of same in the bending plane, and then the bending angle value and the length value of a distal structural body 11 can be obtained according to the distribution radii and the lengths of distal structural backbones 113 and proximal structural backbones 163.

Further, the position sensor 193 uses a slider linear position sensor, and a sliding block 194 in the position sensor 193 is securely connected to the proximal feedback structural backbone 195.

Embodiment III

Figure 9:
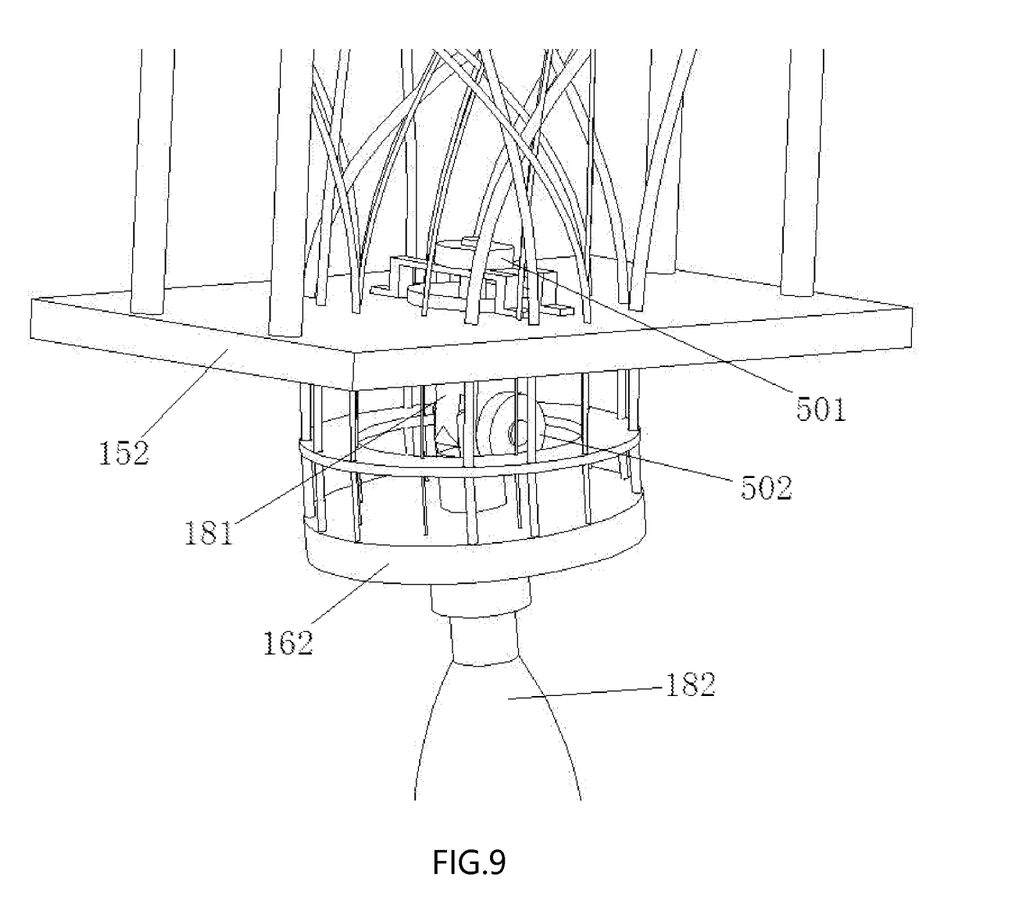
FIG. 9 is a structural schematic diagram of a third posture measurement assembly according to the present invention.

As shown in FIG. 9, a posture measurement assembly in this embodiment comprises a first joint angle sensor 501 and a second joint angle sensor 502, wherein the first joint angle sensor 501 is used for measuring the relative rotation angle between a rotating base 181 and a proximal guide channel fixing plate 152, and thus a bending plane orientation angle of a proximal structural body 16 can be further obtained; and the second joint angle sensor 502 is used for measuring the relative rotation angle between a driving handle 182 and the rotating base 181, and thus the bending angle of the proximal structural body 16 in the above bending plane can be obtained. A bending angle value of the proximal structural body 16 can be obtained according to the angle measured above, and then a bending angle value of a distal structural body 11 can be obtained according to the distribution radii of distal structural backbones 113 and proximal structural backbones 163.

Embodiment IV

Figure 10:
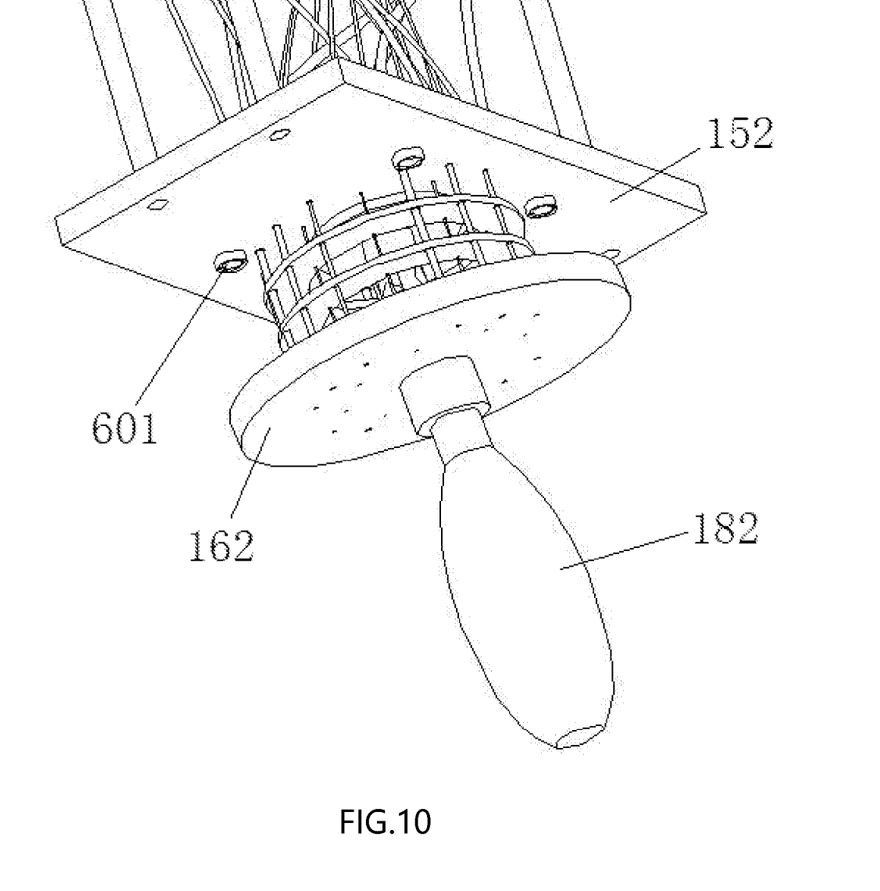
FIG. 10 is a structural schematic diagram of a fourth posture measurement assembly according to the present invention.

As shown in FIG. 10, the posture measurement assembly in this embodiment comprises three or more distance sensors 601 mounted on a proximal guide channel fixing plate 152 for measuring the distance of specific points on a proximal fixation disk 162. The distance sensor 601 can be selected from infrared, laser and other optical distance sensors, and by means of measuring the distance from at least three specific points on the proximal fixation disk 162 to the proximal guide channel fixing plate 152, the orientation and position of the proximal fixation disk 162 relative to the proximal guide channel fixing plate 152 can be obtained, so as to obtain a bending angle value and a length value of a proximal structural body 16, and then a bending angle value and a length value of a distal structural body 11 can be obtained according to the distribution radii and the lengths of distal structural backbones 113 and proximal structural backbones 163.

The present invention has been illustrated only by the above embodiments, and the structure, arrangement position and connection of the components can be varied. On the basis of the technical solutions of the present invention, the improvements or equivalent changes to individual components according to the principles of the present invention should not be excluded from the scope of protection of the present invention.

The invention claimed is:

1. A flexible continuum structure capable of realizing a posture feedback, the flexible continuum comprising a flexible continuum structure body and a posture feedback mechanism; and, wherein
the flexible continuum structure body comprises a distal structural body, a proximal structural body and a middle connecting body, wherein
the distal structural body comprises distal spacing disks, a distal fixation disk and distal structural backbones;
the proximal structural body comprises proximal spacing disks, a proximal fixation disk and proximal structural backbones, the proximal structural backbones being securely connected, in one-to-one correspondence, to or being the same as the distal structural backbones;
the middle connecting body comprises a proximal guide channel fixing plate, a distal guide channel fixing plate and a structural backbone guide channel, the structural backbone guide channel being securely connected between the proximal guide channel fixing plate and the distal guide channel fixing plate, wherein
one end of the proximal structural backbones is securely connected to the proximal fixation disk, and the other end passes through the proximal spacing disks, the structural backbone guide channel and the distal spacing disks in sequence and is then securely connected to the distal fixation disk;
the posture feedback mechanism comprises one or more of an identical posture feedback structure, a first proportional feedback structure and a second proportional feedback structure, wherein
the identical posture feedback structure comprises second distal spacing disks, a second distal fixation disk, second distal structural backbones, second proximal structural backbones and a second structural backbone guide channel, wherein
the second structural backbone guide channel is securely connected between the proximal guide channel fixing plate and the distal guide channel fixing plate,
the second proximal structural backbones are securely connected, in one-to-one correspondence, to or are the same as the second distal structural backbones,
one end of the second structural backbone is securely connected to the proximal fixation disk, and the other end passes through the proximal spacing disks, the second structural backbone guide channel and the second distal spacing disks in sequence and is then securely connected to the second distal fixation disk;
a ratio of a distribution radius of the second distal structural backbone to that of the second proximal structural backbone is consistent with a ratio of the distribution radius of the distal structural backbone to that of the proximal structural backbone;
a length of the identical posture feedback structure is consistent with that of the distal structural body;
the first proportional feedback structure comprises third distal spacing disks, a third distal fixation disk, third distal structural backbones, third proximal structural backbones and a third structural backbone guide channel, wherein
the third structural backbone guide channel is securely connected between the proximal guide channel fixing plate and the distal guide channel fixing plate,
the third proximal structural backbones are securely connected, in one-to-one correspondence, to or are the same as the third distal structural backbones,
one end of the third structural backbone is securely connected to the proximal fixation disk, and the other end passes through the proximal spacing disks, the third structural backbone guide channel and the third distal spacing disks in sequence and is then securely connected to the third distal fixation disk;
a ratio of the distribution radius of the third distal structural backbone to that of the third proximal structural backbone is different from the ratio of the distribution radius of the distal structural backbone to that of the proximal structural backbone;
the second proportional feedback structure comprises fourth distal spacing disks, a fourth distal fixation disk, fourth distal structural backbones, fourth proximal structural backbones and a fourth structural backbone guide channel, wherein
the fourth structural backbone guide channel is securely connected between the proximal guide channel fixing plate and the distal guide channel fixing plate,
the fourth proximal structural backbones are securely connected, in one-to-one correspondence, to or are the same as the fourth distal structural backbones,
one end of the fourth structural backbone is securely connected to the proximal fixation disk, and the other end passes through the proximal spacing disks, the fourth structural backbone guide channel and the fourth distal spacing disks in sequence and is then securely connected to the fourth distal fixation disk, and
each of the fourth distal structural backbones and the corresponding fourth proximal structural backbone, which have a connection relationship, have spacing angles on a circumference between each other, with a degree of the spacing angles being the same.

2. The flexible continuum structure capable of realizing a posture feedback according to claim 1, wherein the flexible continuum structure body further comprises an articulated driving chain comprising a rotating base and a driving handle, the rotating base being rotatably connected in the center of the proximal guide channel fixing plate, and an axis of rotation of the rotating base being perpendicular to the proximal guide channel fixing plate, wherein
    the driving handle is of a rod structure and a front end thereof is rotatably connected to the rotating base,
    the axis of rotation of the driving handle is parallel to the proximal guide channel fixing plate, and
    the driving handle slidably and rotatably passes through the center of the proximal fixation disk.

3. The flexible continuum structure capable of realizing a posture feedback according to claim 2, wherein the posture feedback mechanism further comprises a posture measurement assembly comprising a first joint angle sensor and a second joint angle sensor, wherein the first joint angle sensor is configured for measuring a relative rotation angle between the rotating base and the proximal guide channel fixing plate, and the second joint angle sensor is configured for measuring the relative rotation angle between the driving handle and the rotating base.

4. The flexible continuum structure capable of realizing a posture feedback according to claim 1, wherein the middle connecting body further comprises a rigid tube, the rigid tube is securely connected to a side of the distal guide channel fixing plate that is close to the distal structural body, the rigid tube is internally provided with a cavity in communication with the structural backbone guide channel, and the structural backbones pass through the cavity.

5. The flexible continuum structure capable of realizing a posture feedback according to claim 4, wherein when the posture feedback mechanism comprises an identical posture feedback structure, the identical posture feedback structure further comprises a second rigid tube, wherein the second structural backbones pass through the second rigid tube; and, wherein
    when the posture feedback mechanism comprises a first proportional feedback structure, the first proportional feedback structure further comprises a third rigid tube, and the third structural backbones pass through the third rigid tube; and
    when the posture feedback mechanism comprises a second proportional feedback structure, the second proportional feedback structure further comprises a fourth rigid tube, and the fourth structural backbones pass through the fourth rigid tube.

6. The flexible continuum structure capable of realizing a posture feedback according to claim 1, wherein the posture feedback mechanism further comprises a posture measurement assembly comprising a distal feedback structural backbone, a feedback structural backbone guide channel and a position sensor, wherein
    the position sensor is securely connected to the proximal guide channel fixing plate, and
    one end of the distal feedback structural backbone is securely connected to the distal fixation disk, and the other end passes through the distal spacing disks and the feedback structural backbone guide channel and is then connected to the position sensor.

7. The flexible continuum structure capable of realizing a posture feedback according to claim 6, wherein a third guide channel fixing plate is provided between the proximal guide channel fixing plate and the distal guide channel fixing plate, wherein the feedback structural backbone guide channel is securely connected between the third guide channel fixing plate and the distal guide channel fixing plate.

8. The flexible continuum structure capable of realizing a posture feedback according to claim 6, wherein the position sensor uses a slider linear position sensor.

9. The flexible continuum structure capable of realizing a posture feedback according to claim 1, wherein the posture feedback mechanism further comprises a posture measurement assembly comprising a proximal feedback structural backbone and a position sensor, wherein the position sensor is securely connected to the proximal guide channel fixing plate, one end of the proximal feedback structural backbone is securely connected to the proximal fixing plate, and the other end passes through the proximal spacing disks and is then connected to the position sensor.

10. The flexible continuum structure capable of realizing a posture feedback according to claim 1, wherein the posture feedback mechanism further comprises a posture measurement assembly comprising three or more distance sensors mounted on the proximal guide channel fixing plate for measuring distance of specific points on the proximal fixation disk.

11. A flexible continuum structure capable of realizing a posture feedback, comprising a flexible continuum structure body and a posture feedback mechanism; and, wherein
    the flexible continuum structure body comprises a distal structural body, a proximal structural body and a middle connecting body, wherein
    the distal structural body comprises distal spacing disks, a distal fixation disk and distal structural backbones;
    the proximal structural body comprises proximal spacing disks, a proximal fixation disk and proximal structural backbones, the proximal structural backbones being securely connected, in one-to-one correspondence, to or being the same as the distal structural backbones;
    the middle connecting body comprises a proximal guide channel fixing plate, a distal guide channel fixing plate and a structural backbone guide channel, and the structural backbone guide channel being securely connected between the proximal guide channel fixing plate and the distal guide channel fixing plate, wherein
        one end of the structural backbone being securely connected to the proximal fixation disk, and the other end passing through the proximal spacing disks, the structural backbone guide channel and the distal spacing disks in sequence and being then securely connected to the distal fixation disk; and
    the posture feedback mechanism comprises one or more of an identical posture feedback structure, a first proportional feedback structure and a second proportional feedback structure, wherein
    the identical posture feedback structure comprises a second distal fixation disk, second distal structural backbones, second proximal structural backbones and a second structural backbone guide channel, wherein
    the second structural backbone guide channel is securely connected between the proximal guide channel fixing plate and the distal guide channel fixing plate,
    the second proximal structural backbones are securely connected, in one-to-one correspondence, to or are the same as the second distal structural backbones,
    one end of the second structural backbone is securely connected to the proximal fixation disk, and the other end passes through the proximal spacing disks and the second structural backbone guide channel in sequence and is then securely connected to the second distal fixation disk;

a ratio of a distribution radius of the second distal structural backbone to that of the second proximal structural backbone is consistent with a ratio of the distribution radius of the distal structural backbone to that of the proximal structural backbone;

the first proportional feedback structure comprises a third distal fixation disk, third distal structural backbones, third proximal structural backbones and a third structural backbone guide channel, wherein the third structural backbone guide channel is securely connected between the proximal guide channel fixing plate and the distal guide channel fixing plate, the third proximal structural backbones are securely connected, in one-to-one correspondence, to or are the same as the third distal structural backbones, one end of the third structural backbone is securely connected to the proximal fixation disk, and the other end passes through the proximal spacing disks and the third structural backbone guide channel in sequence and is then securely connected to the third distal fixation disk;

a ratio of the distribution radius of the third distal structural backbone to that of the third proximal structural backbone is different from the ratio of the distribution radius of the distal structural backbone to that of the proximal structural backbone;

the second proportional feedback structure comprises a fourth distal fixation disk, fourth distal structural backbones, fourth proximal structural backbones and a fourth structural backbone guide channel;

the fourth structural backbone guide channel is securely connected between the proximal guide channel fixing plate and the distal guide channel fixing plate, the fourth proximal structural backbones are securely connected, in one-to-one correspondence, to or are the same as the fourth distal structural backbones, one end of the fourth structural backbone is securely connected to the proximal fixation disk, and the other end passes through the proximal spacing disks and the fourth structural backbone guide channel in sequence and is then securely connected to the fourth distal fixation disk; and each of the fourth distal structural backbones and the corresponding fourth proximal structural backbone, which have a connection relationship, have spacing angles on a circumference between each other, with a degree of the spacing angles being the same.

12. The flexible continuum structure capable of realizing a posture feedback according to claim 11, wherein when the posture feedback mechanism comprises an identical posture feedback structure, the identical posture feedback structure is further provided with second distal spacing disks, and the other end of the second structural backbone further passes through the second distal spacing disks after passing through the second structural backbone guide channel and is then securely connected to the second distal fixation disk;

when the posture feedback mechanism comprises a first proportional feedback structure, the first proportional feedback structure is further provided with third distal spacing disks, and the other end of the third structural backbone further passes through the third distal spacing disks after passing through the third structural backbone guide channel and is then securely connected to the third distal fixation disk; and when the posture feedback mechanism comprises a second proportional feedback structure, the second proportional feedback structure is further provided with fourth distal spacing disks, and the other end of the fourth structural backbone further passes through the fourth distal spacing disks after passing through the fourth structural backbone guide channel and is then securely connected to the fourth distal fixation disk.

13. The flexible continuum structure capable of realizing a posture feedback according to claim 11, wherein when the posture feedback mechanism comprises an identical posture feedback structure, the identical posture feedback structure is further provided with second distal spacing disks, and the other end of the second structural backbone further passes through the second distal spacing disks after passing through the second structural backbone guide channel and is then securely connected to the second distal fixation disk; and a length of the identical posture feedback structure is consistent with that of the distal structural body.

14. The flexible continuum structure capable of realizing a posture feedback as according to claim 11, wherein the flexible continuum structure body further comprises an articulated driving chain comprising a rotating base and a driving handle, the rotating base being rotatably connected in the center of the proximal guide channel fixing plate, and an axis of rotation of the rotating base being perpendicular to the proximal guide channel fixing plate, wherein the driving handle is of a rod structure and a front end thereof is rotatably connected to the rotating base, the axis of rotation of the driving handle is parallel to the proximal guide channel fixing plate, and the driving handle slidably and rotatably passes through the center of the proximal fixation disk.

15. The flexible continuum structure capable of realizing a posture feedback according to claim 11, wherein the middle connecting body further comprises a rigid tube, the rigid tube is securely connected to a side of the distal guide channel fixing plate that is close to the distal structural body, the rigid tube is internally provided with a cavity in communication with the structural backbone guide channel, and the structural backbone passes through the cavity.

16. A flexible continuum structure capable of realizing a posture feedback, wherein the flexible continuum structure comprises a flexible continuum structure body and a posture feedback mechanism, wherein, the flexible continuum structure body comprises a distal structural body, a proximal structural body and a middle connecting body, wherein the distal structural body comprises distal spacing disks, a distal fixation disk and distal structural backbones;

the proximal structural body comprises proximal spacing disks, a proximal fixation disk and proximal structural backbones, the proximal structural backbones being securely connected, in one-to-one correspondence, to or being the same as the distal structural backbones;

the middle connecting body comprises a proximal guide channel fixing plate, a distal guide channel fixing plate and a structural backbone guide channel, wherein the structural backbone guide channel is securely connected between the proximal guide channel fixing plate and the distal guide channel fixing plate, one end of the structural backbone being securely connected to the proximal fixation disk, and the other end passing through the proximal spacing disks, the structural backbone guide channel and the distal spacing disks in sequence and being then securely connected to the distal fixation disk; and the posture feedback mechanism comprises a posture measurement assembly, which is configured to be able to detect a bending angle value and a length value of the distal structural body.

17. The flexible continuum structure capable of realizing a posture feedback according to claim 16, wherein the posture measurement assembly comprises a distal feedback structural backbone, a feedback structural backbone guide channel and a position sensor, wherein the position sensor is securely connected to the proximal guide channel fixing plate, one end of the distal feedback structural backbone is securely connected to the distal fixation disk, and the other end passes through the distal spacing disks and the feedback structural backbone guide channel and is then connected to the position sensor.

18. The flexible continuum structure capable of realizing a posture feedback according to claim 16, wherein the posture measurement assembly comprises a proximal feedback structural backbone and a position sensor, the position sensor is securely connected to the proximal guide channel fixing plate, one end of the proximal feedback structural backbone is securely connected to the proximal fixing plate, and the other end passes through the proximal spacing disks and is then connected to the position sensor.

19. The flexible continuum structure capable of realizing a posture feedback according to claim 16, wherein the flexible continuum structure body further comprises an articulated driving chain, which comprising a rotating base and a driving handle, with the rotating base being rotatably connected in the center of the proximal guide channel fixing plate, and an axis of rotation of the rotating base being perpendicular to the proximal guide channel fixing plate; and the driving handle is rotatably connected to the rotating base, the axis of rotation of which is parallel to the proximal guide channel fixing plate, and the driving handle slidably and rotatably passes through the center of the proximal fixation disk.

20. The flexible continuum structure capable of realizing a posture feedback according to claim 19, wherein the posture feedback mechanism comprises a first joint angle sensor and a second joint angle sensor, wherein the first joint angle sensor is used for measuring a relative rotation angle between the rotating base and the proximal guide channel fixing plate, and the second joint angle sensor is used for measuring the relative rotation angle between the driving handle and the rotating base.

* * * * *